(12) United States Patent
Oyama et al.

(10) Patent No.: US 8,859,212 B2
(45) Date of Patent: Oct. 14, 2014

(54) METHOD OF EXTRACTING FOOD COMPONENT, FOOD INSPECTION METHOD AND FOOD INSPECTION KIT

(75) Inventors: Yuriko Oyama, Yokohama (JP); Tsutomu Honjoh, Yokohama (JP); Masatoshi Sakai, Yokohama (JP); Eriko Watanabe, Yokohama (JP); Kaori Itoh, Yokohama (JP); Rieko Tsuruma, Yokohama (JP)

(73) Assignee: Morinaga & Co., Ltd., Tokyo (JP)

( * ) Notice: Subject to any disclaimer, the term of this patent is extended or adjusted under 35 U.S.C. 154(b) by 631 days.

(21) Appl. No.: 12/744,832

(22) PCT Filed: Nov. 28, 2008

(86) PCT No.: PCT/JP2008/071716
§ 371 (c)(1),
(2), (4) Date: May 26, 2010

(87) PCT Pub. No.: WO2009/069779
PCT Pub. Date: Jun. 4, 2009

(65) Prior Publication Data
US 2010/0304499 A1 Dec. 2, 2010

(30) Foreign Application Priority Data
Nov. 30, 2007 (JP) ................. 2007-309930

(51) Int. Cl.
*G01N 33/53* (2006.01)
*G01N 33/558* (2006.01)
*G01N 33/02* (2006.01)
*G01N 33/68* (2006.01)

(52) U.S. Cl.
CPC ............. *G01N 33/558* (2013.01); *G01N 33/02* (2013.01); *G01N 2333/415* (2013.01); *G01N 2333/4731* (2013.01); *G01N 33/68* (2013.01)
USPC ............................ 435/7.1; 435/7.92; 436/501

(58) Field of Classification Search
None
See application file for complete search history.

(56) References Cited

U.S. PATENT DOCUMENTS

| 4,302,200 A | 11/1981 | Yokoyama et al. |
| 6,004,930 A * | 12/1999 | Hainline .................. 514/5.5 |
| 2012/0020992 A1* | 1/2012 | Heifetz et al. ............ 424/192.1 |
| 2012/0095190 A1* | 4/2012 | Deak et al. .................. 530/378 |

FOREIGN PATENT DOCUMENTS

| DE | 10 2004 029 887 | 1/2005 |
| JP | 55-26817 | 2/1980 |
| JP | 9-37720 | 2/1997 |
| JP | 2006-71509 | 3/2006 |
| JP | 2006-317226 | 11/2006 |
| JP | 2007-278773 | * 10/2007 ........... G01N 33/543 |
| WO | 2004/000032 | 12/2003 |

OTHER PUBLICATIONS

International Search Report for International Application No. PCT/JP2008/071716 mailed Dec. 22, 2008.
Itoh et al.; "Effects of Inorganic Reducing Agents on the Gel Formation of Fish Meat by Heating" Bulletin of the Japanese Society of Scientific Fisheries; 1979; vol. 45; No. 4; pp. 455-458.
Extended European Search Report for Application No. EP 08 85 3849 dated Oct. 21, 2011.

* cited by examiner

*Primary Examiner* — Gary W Counts
(74) *Attorney, Agent, or Firm* — Smith, Gambrell & Russell LLP

(57) ABSTRACT

Provided is a technique of extracting a component in a food from the food by using a reducing agent that is inexpensive and has a mild reducing action. A component in a food is extracted by mixing the food with an extractant containing a sulfite. In addition, the resultant food extract is brought into contact with a specific antibody that specifically recognizes a substance included in a specified ingredient of interest for inspection, to thereby inspect the presence or absence and/or the amount of a specified ingredient in a food by utilizing an immunological measurement method. Further provided is a food inspection kit for inspection of the presence or absence and/or the amount of a specified ingredient in a food, including: (1) an extractant and a sulfite to be added to the extractant, or an extractant including a sulfite added; and (2) an antibody that specifically recognizes a substance included in a specified ingredient of interest for inspection.

7 Claims, 2 Drawing Sheets

METHOD OF EXTRACTING FOOD COMPONENT, FOOD INSPECTION METHOD AND FOOD INSPECTION KIT

TECHNICAL FIELD

The present invention relates to a food component extraction method, a food inspection method, and a food inspection kit each used for inspection of the presence or absence and/or the amount of a specified ingredient in a food.

BACKGROUND ART

In recent years, in response to increasing concern of consumers about food allergy problems, it is recommended to provide food packages or the like with labels indicating that ingredients which cause food allergy are contained. In particular, with regard to seven items consisting of wheat, buckwheat, eggs, milk, peanuts, shrimps, and crabs, all of which are to be highly required to label in consideration of the number of cases of allergy and their seriousness, thus mandatory labeling of foods containing those ingredients is required for manufacturers under the Food Sanitation Law as well.

Further, labeling indicating "containing a specified ingredient", "containing no specified ingredient", or the like provides a benefit for manufacturers as well because the labeling allows consumers to receive their products without anxiety.

In a processed food to be manufactured by mixing various ingredients, since tracing of records for individual ingredients is complicated, it is desirable to be able to directly inspect a manufactured product. Further, the contamination of a substance, which is not used as an ingredient, may occur in a manufacturing line. Thus, from the viewpoints of the operation and maintenance of a product and the prevention of an unforeseen accident, there is a demand to provide a food inspection method that can be utilized in a quick and simple manner even in manufacturing plants, and that can detect with good accuracy whether a food contains a specified ingredient or not.

In the case of a processed food, even in a component derived from the same ingredient, there is a problem in that, in some manufacturing conditions, a substance contained in a specified ingredient of interest for inspection is insolubilized and hence is hardly extracted. In baked confectionery and the like, a protein is hardly extracted because heating denatures the protein and thiol groups form an S—S bond. Further, it is also conceivable that a substance contained in a specified ingredient of interest for inspection interacts with other components compounded in a processed food, and is insolubilized, resulting in poor extraction efficiency.

The poor extraction efficiency during preparation of an extract from a food is not preferred in consideration of a demand to detect a specified ingredient of interest for inspection with good accuracy. Further, it is also conceivable that the poor extraction efficiency generates variations in the inspection results.

In order to deal with the above-mentioned problems, for example, Patent Document 1 below discloses an invention of a food component extractant characterized by containing a reducing agent and a solubilizer. Further, the patent document describes that the incorporation of a reducing agent for changing a protein structure, and a solubilizer made up of a surfactant, urea, and the like into an extractant enables a denatured and/or non-denatured protein to be extracted with higher efficiency than ever before.

In addition, there is known, in immunochromatography out of immunological measurement methods, a phenomenon called a "prozone phenomenon" in which a measurement value is lowered when a substance (antigen) of interest for inspection exists in an excessive amount with respect to the amount of an antibody to be used. Owing to the prozone phenomenon, there has been a problem in that, when a sample contains a substance (antigen) of interest for inspection in a large amount, the sample may be evaluated as false negative, with the result that the evaluation lacks reliability.

Patent Document 1: JP-A-2006-71509

DISCLOSURE OF THE INVENTION

Problems to be Solved by the Invention

However, although Patent Document 1 above exemplifies, as a reducing agent, 2-mercaptoethanol, dithiothreitol, or tris (2-carboxyethyl)phosphine), 2-mercaptoethanol or dithiothreitol has been difficult to use in processed food manufacturing plants because of its irritating odor. Further, tris(2-carboxyethyl)phosphine or its analogous reducing agent, tris (3-hydroxypropyl)phosphine, or the like is a relatively expensive reagent and hence is disadvantageous in terms of cost. In addition, those reducing agents have a relatively strong reducing action, and hence, the adhesion of a highly concentrated solution thereof to the skin mucosa causes an inflammation and a burn. Therefore, the reducing agents have also been difficult to use in processed food manufacturing plants from the viewpoints of workers' safety.

Thus, objects of the present invention are to provide a technique of extracting a component in a food from the food by using a reducing agent that is inexpensive and has a mild reducing action, and to provide a technique of suppressing a prozone phenomenon in food inspection measurement for inspection of the presence or absence and/or the amount of a specified ingredient in a food by utilizing immunochromatography.

Means for Solving the Problems

The inventors of the present invention have intensively studied in order to accomplish the above-mentioned objects. As a result, the inventors have focused attention on using, as a reducing agent for extracting a component from a food, a sulfite such as sodium sulfite which is a commonly used food additive. Thus, the present invention has been completed.

That is, a food component extraction method of the present invention is characterized by including: mixing a food with an extractant including a sulfite; and extracting a component in the food.

According to the food component extraction method of the present invention, even in a component in a food made up of a protein or the like, which has been denatured by baking or the like to form an S—S bond, a sulfite may enhance the solubility of the component to improve extraction efficiency. Further, in the case of a food in a liquid form or in an emulsion form, the solubilization of solid contents in the food may be promoted. In addition, the method is easily employed even in processed food manufacturing plants because there is no odor.

In the food component extraction method of the present invention, it is preferred that the extractant include a surfactant. In this case, the surfactant is preferably sodium dodecyl sulfate. According to this aspect, because the extractant contains a surfactant, the extraction efficiency of a component in a food may be increased synergistically.

Meanwhile, a food inspection method of the present invention is a food inspection method for inspection of the presence or absence and/or the amount of a specified ingredient in a food, characterized by including: bringing a food into contact with an extractant including a sulfite to prepare a food extract in which a component in the food is extracted; then bringing the food extract into contact with a specific antibody that specifically recognizes a substance included in a specified ingredient of interest for inspection; and inspecting the presence or absence and/or the amount of a specified ingredient in a food by utilizing an immunological measurement method.

According to the food inspection method of the present invention, because the extractant contains a sulfite, even in a component in a food made up of a protein or the like, which has been denatured by baking or the like to form an S—S bond, a sulfite may enhance the solubility of the component to improve extraction efficiency. Further, in the case of a food in a liquid form or in an emulsion form, the solubilization of solid contents in the food may be promoted. In addition, the method is easily employed even in processed food manufacturing plants because there is no odor.

In the food inspection method of the present invention, the immunological measurement method is preferably a method using immunochromatography. Accordingly, the food inspection method of the present invention may be employed very easily without the need of a special device. Further, it is preferred that the specific antibody be labeled with a metal colloid. Accordingly, immunological measurement results may be visibly judged by the metal colloid label.

Further, a food inspection method of the present invention in which a prozone phenomenon is suppressed, including: bringing a food into contact with an extractant to prepare a food extract in which a component in the food is extracted; then bringing the food extract into contact with a specific antibody that specifically recognizes a substance included in a specified ingredient of interest for inspection; and inspecting the presence or absence and/or the amount of the specified ingredient in the food by utilizing an immunological measurement method, is characterized in that: immunochromatography is used as the immunological measurement method; and a prozone phenomenon during food inspection measurement is suppressed by incorporating sodium dodecyl sulfate and a sulfite into the food extract.

According to the food inspection method of the present invention in which a prozone phenomenon is suppressed, when the presence or absence and/or the amount of a specified ingredient in a food is inspected by utilizing immunochromatography, through the incorporation of sodium dodecyl sulfate and a sulfite into a food extract, which is subjected to immunochromatography, the detectability may be maintained in low concentrated regions in which a substance (antigen) of interest for inspection exists in a food extract in a relatively small amount, while a prozone phenomenon may be prevented in highly concentrated regions in which a substance (antigen) of interest for inspection exists in a food extract in a relatively large amount. This allows reliable food inspection measurement in a wide range of concentration regions.

Further, in the food inspection method of the present invention in which a prozone phenomenon is suppressed, the sulfite is preferably at least one kind selected from sodium sulfite, sodium hydrogen sulfite, potassium sulfite, ammonium sulfite, and iron sulfite.

Further, in the food inspection method of the present invention in which a prozone phenomenon is suppressed, it is preferred that the specified ingredient of interest for inspection be wheat, and the specific antibody be a specific antibody to gliadin. In this case, the food extract, which is subjected to the immunochromatography, contains gliadin in a concentration of preferably 10 ng/ml to 100 μg/ml.

Further, in the food inspection method of the present invention in which a prozone phenomenon is suppressed, it is preferred that the specified ingredient of interest for inspection be milk, and the specific antibody be a specific antibody to casein. In this case, the food extract, which is subjected to the immunochromatography, contains casein in a concentration of preferably 50 ng/ml to 100 μg/ml.

Meanwhile, a food inspection kit of the present invention is a food inspection kit for inspection of the presence or absence and/or the amount of a specified ingredient in a food, and is characterized by including: (1) an extractant and a sulfite to be added to the extractant, or an extractant including a sulfite added; and (2) an antibody that specifically recognizes a substance included in a specified ingredient of interest for inspection.

According to the food inspection kit of the present invention, food inspection may be performed at a low cost by using, as a reducing agent, a sulfite which is a food additive.

In the food inspection kit of the present invention, it is preferred that the kit include, as a sulfite, at least one kind selected from sodium sulfite, sodium hydrogen sulfite, potassium sulfite, ammonium sulfite, and iron sulfite. Further, it is preferred that the antibody be bound to an immunochromatograph. Further, it is preferred that the food inspection kit further include sodium dodecyl sulfate as a constituent element of the kit.

Effects of the Invention

According to the present invention, a sulfite such as sodium sulfite which is a commonly used food additive is used as a reducing agent for extracting a component from a food, and hence the sulfite is safe and easily used even in processed food manufacturing plants. Further, the extraction for food inspection may be performed at a low cost because the sulfite is an inexpensive reducing agent. Moreover, even if a sulfite contained in an extractant still remains during measurement of the formation of an immune complex with a specific antibody, the measurement is not adversely affected. In addition, in measurement utilizing immunochromatography, the detectability may be maintained in low concentrated regions in which a substance (antigen) of interest for inspection exists in a relatively small amount, while a prozone phenomenon may be prevented in highly concentrated regions in which a substance (antigen) of interest for inspection exists in a relatively large amount. This allows reliable measurement in a wide range of concentration regions.

BEST MODE FOR CARRYING OUT THE INVENTION

The food component extraction method of the present invention involves mixing a food with an extractant containing a sulfite, and extracting a component in the food. A substance contained in a specified ingredient (hereinafter, referred to as "substance of interest for inspection") is transferred into the extractant together with other components. The form of a food to be inspected may be any one of a solid form, a semisolid form, a jelly form, a liquid form, and an emulsion form. The sulfite in the extractant may enhance the solubility of a component in a food to improve extraction efficiency because the sulfite may reduce an S—S bond in a protein or the like to produce a free SH group. Further, in the case of a food in a liquid form or an emulsion form, the solubilization of solid contents in the food may be promoted.

A preferred example of the sulfite to be used in the food component extraction method of the present invention includes sodium sulfite which is a commonly used food additive. The sulfite may be used in a combination of two or more kinds thereof.

The concentration of the sulfite to be used in the food component extraction method of the present invention in the extractant may be appropriately adjusted depending on characteristics of a food to be inspected or a "substance of interest for inspection". For example, when sodium sulfite is used as the reducing agent, it is recommended that the concentration be adjusted to about 0.0001 to 1 M, preferably 0.005 to 0.5 M, or more preferably 0.05 to 0.2 M.

Further, a solubilizing aid for aiding the solubilization of a component in a food may be added to the above-mentioned extractant. Examples of the solubilizing aid which may be used include generally commonly used solubilizing aids such as sodium dodecyl sulfate (hereinafter, referred to as SDS), urea, and a nonionic surfactant. The solubilizing aid may be used in a combination of two or more kinds thereof.

The concentration of the above-mentioned solubilizing aid in the extractant may be appropriately adjusted depending on characteristics of a food to be inspected or a "substance of interest for inspection". For example, when SDS is used as the solubilizing aid, it is recommended that the concentration be adjusted to about 0.01 to 10 w/v %, preferably 0.03 to 5 w/v %, or more preferably 0.1 to 1 w/v %.

In the food component extraction method of the present invention, the above-mentioned extractant is prepared by dissolving the above-mentioned sulfite or both the above-mentioned sulfite and the above-mentioned solubilizing aid in an aqueous solvent. For an aqueous medium, water or a generally commonly used phosphate buffer, Tris-HCl buffer may be used, for example. Further, taking the facilitation of operations after the extraction into consideration, the pH of the above-mentioned extractant is generally preferably adjusted to pH 6 to 8.5.

For example, well-known means such as stirring, mixing, centrifugation, and filtration may be appropriately used for extraction to prepare a food extract. In this case, it is desired that a food be pulverized or formed into a paste to increase a contact area with the extractant, and mixing be performed in a contact state. This allows extraction efficiency to be increased. Further, in this case, the mass ratio of a food to an extractant is preferably 10 to 100 of the extractant with respect to 1 of the food. This allows a highly concentrated food extract to be prepared. In the food extract extracted as described above, a "substance of interest for inspection" in a food is transferred into the extract together with other components. Here, in the present invention, the substance of interest for inspection is not necessarily only one kind. Instead, two or more substances of interest for inspection may be used with respect to one specified ingredient.

Meanwhile, the food inspection method of the present invention is a food inspection method for inspection of the presence or absence and/or the amount of a specified ingredient in a food by using a specific antibody that specifically recognizes a "substance of interest for inspection".

In the food inspection method of the present invention, first, a component in a food is extracted from the food by the above-mentioned method to prepare a food extract. It should be noted that, as described later, an immune complex of a "substance of interest for inspection" and a specific antibody must be formed. Thus, various conditions such as a salt concentration, a pH, a temperature, and a time during preparation of the above-mentioned food extract must be set in such a range that the "substance of interest for inspection" does not lose the antigenicity to the specific antibody.

Then, the obtained food extract is brought into contact with a specific antibody that specifically recognizes a "substance of interest for inspection". As a result, an immune complex is formed by a binding mechanism of a well-known antigen-antibody reaction. Here, the above-mentioned food extract is a concept that includes a preparation which is appropriately subjected to a treatment such as dilution, concentration, and pH adjustment so as to achieve an optimum condition for formation of an immune complex and for an immunological measurement method as described later. An immunological measurement method of measuring the formation of the immune complex as described above can detect the presence of a "substance of interest for inspection", and besides can inspect the presence or absence and/or the amount of a specified ingredient in a food.

The preparation of a specific antibody that specifically recognizes a specified substance is well known to one skilled in the art. For example, Patent Document 1 (JP-A-2003-294737) above discloses "an IgG fraction or a polyclonal antibody of a serum obtained from a serum of a mammal immunized with an antigen mainly formed of a protein fraction corresponding to 70 to 500 kD of buckwheat", Patent Document 2 (JP-A-2003-294738) above discloses "an IgG fraction or a polyclonal antibody of a serum obtained from a serum of a mammal immunized with an antigen mainly formed of a protein fraction corresponding to 30 to 100 kD of peanuts", and Patent Document 3 (JP-A-2003-294748) above discloses "an antibody obtained from a serum of a mammal immunized with an albumen-derived protein". Such well-known technique may be used to prepare a specific antibody that specifically recognizes a "substance of interest for inspection".

In the food inspection method of the present invention, the formation of an immune complex using a specific antibody may be measured by a well-known immunological measurement method. There is known, as the immunological measurement method, an ELISA method and immunochromatography. Of those, immunochromatography is preferably used because there is no need to use a measurement instrument, immunological measurement results may be visually judged in a simple manner, and the speed is quick and the sensitivity is also high. The principle of immunochromatography is well known to one skilled in the art as described in JP-A-05-5743 and JP-A-2002-202307 as well.

However, one example of the principle is briefly described for confirmation. A first specific antibody is immobilized in a band form in a specified region (test line position) in a thin film support such as a cellulose membrane, and a labeled second specific antibody is retained in a movable manner at a sample dropping portion or its adjacent downstream in the other regions. Hereinafter, in the present invention, an antibody-supported carrier constructed as described above is referred to as an "immunochromatograph".

When an analysis target is dropped to a sample dropping portion together with a solvent for the analysis target, the analysis target and the labeled second specific antibody are developed in the thin film support by a capillary phenomenon. If the analysis target contains a "substance of interest for inspection", the second specific antibody, which has been developed in the same manner as the analysis target during development of the analysis target in the thin film support, binds to a "substance of interest for inspection". Here, the second specific antibody is preliminarily bound to a colored or coloring substance as a label, and thus, the "substance of interest for inspection" binds to the label. After that, the "substance of interest for inspection" binds to a first specific antibody immobilized at a test line position, and the first specific antibody binds to the second specific antibody like a sandwich across the "substance of interest for inspection". As a result, because the labels gather together at the test line position, it looks as if a band appears at the test line position. Through the band appearance, it is judged that the "substance of interest for inspection" exists in the analysis target. Meanwhile, when the analysis target contains no "substance of interest for inspection" or contains a "substance of interest for inspection" in only an amount equal to or less than the detection limit, a band does not appear at the test line position. The immunochromatography is a quick and simple method, which takes about 5 to 15 minutes after the analysis target has been dropped to a sample dropping portion.

Examples of the above-mentioned label which may be used include a metal colloid, an enzyme label, colored latex particles, and carbon particles, and a gold colloid is preferred in terms of easiness in labeling of an antibody.

Here, the reason why a prozone phenomenon occurs in the immunochromatography is probably because a substance (antigen) of interest excessively exists, and hence binds to the above-mentioned first specific antibody and second specific antibody in a supersaturating state, which inhibits the formation of a sandwich structure across the "substance of interest for inspection" at the test line position.

In the food inspection method of the present invention in which a prozone phenomenon is suppressed, it is preferred to preliminarily incorporate sodium dodecyl sulfate and a sulfite into an extractant to be brought into contact with a food. Furthermore, it is recommended that sodium dodecyl sulfate and a sulfite be incorporated into a food extract, which is subjected to immunochromatography.

Further, the amount of sodium dodecyl sulfate is adjusted so that the concentration thereof in the food extract, which is subjected to immunochromatography, comes to preferably about 0.01 to 5 w/v %, more preferably about 0.02 to 3 w/v %, or most preferably about 0.02 to 1 w/v %. The concentration less than the above-mentioned range is not preferred because an effect of suppressing a prozone phenomenon is poor. Further, the concentration more than the above-mentioned range is not preferred because the detectability by immunochromatography may be impaired on the contrary. For adjustment to the above-mentioned concentration, it is recommended that the above-mentioned extract be appropriately diluted with, for example, aqueous media such as water, a generally commonly used phosphate buffer, or a Tris-HCl buffer. The dilution magnification is preferably 5- to 20-fold.

Meanwhile, the amount of the sulfite is adjusted so that the concentration thereof in a food extract, which is subjected to immunochromatography, comes to preferably about 0.0001 to 1 M, more preferably about 0.001 to 0.1 M, or most preferably about 0.005 to 0.03 M. The concentration less than the above-mentioned range is not preferred because an effect of solubilizing a substance (antigen) of interest for inspection stably from a processed food is poor. Further, the concentration more than the above-mentioned range is not preferred because the detectability by immunochromatography may be impaired on the contrary. For adjustment to the above-mentioned concentration, it is recommended that the above-mentioned extract be appropriately diluted with, for example, aqueous media such as water, a generally commonly used phosphate buffer, or a Tris-HCl buffer. The dilution magnification is preferably 5- to 20-fold.

Examples of the sulfite to be used in the food inspection method of the present invention in which a prozone phenomenon is suppressed include sodium sulfite, sodium hydrogen sulfite, potassium sulfite, ammonium sulfite, and iron sulfite. Further, preferred examples include sodium sulfite which is a commonly used food additive. Those sulfites may be used in a combination of two or more kinds thereof.

The food inspection method of the present invention in which a prozone phenomenon is suppressed is preferably applied when a specified ingredient of interest for inspection is wheat, and a specific antibody to gliadin is used as a specific antibody, for example. In this case, the food extract, which is subjected to immunochromatography, contains gliadin in a concentration of preferably 10 ng/ml to 100 µg/ml, more preferably 100 ng/ml to 100 µg/ml, or most preferably 10 µg/ml to 100 µg/ml. The concentration less than the above-mentioned range is not preferred because the detection becomes difficult. Further, the concentration more than the above-mentioned range is not preferred because the detectability by immunochromatography may be impaired on the contrary.

The food inspection method of the present invention in which a prozone phenomenon is suppressed is preferably applied when a specified ingredient of interest for inspection is milk, and a specific antibody to casein is used as a specific antibody, for example. In this case, the food extract, which is subjected to immunochromatography, contains casein in a concentration of preferably 50 ng/ml to 100 µg/ml, or more preferably 10 µg/ml to 100 µg/ml. The concentration less than the above-mentioned range is not preferred because the detection becomes difficult. Further, the concentration more than the above-mentioned range is not preferred because the detectability by immunochromatography may be impaired on the contrary.

Meanwhile, the food inspection kit of the present invention may be suitably used for a method for inspection of the presence or absence and/or the amount of a specified ingredient in a food. In particular, the food inspection kit may be preferably used for the above-mentioned food inspection method of the present invention.

Examples of the sulfite to be used in the food inspection kit of the present invention include sodium sulfite, sodium hydrogen sulfite, potassium sulfite, ammonium sulfite, and iron sulfite. Preferred is sodium sulfite which is a commonly used food additive. The sulfite may be used in a combination of two or more kinds thereof. The sulfite, which has been dissolved in a solvent such as water or a buffer, may be supplied to the food inspection kit of the present invention.

The food inspection kit of the present invention may further include sodium dodecyl sulfate as a constituent element of the kit. Sodium dodecyl sulfate, which has been dissolved in a solvent such as water or a buffer, may be supplied to the food inspection kit of the present invention.

In the food inspection kit of the present invention, an antibody that specifically recognizes a substance contained in a specified ingredient of interest for inspection is desirably bound to an immunochromatograph. Here, the term "bound" means that two or more objects are bonded to each other and are in such a state that their separation can be achieved only by destruction or payment of excessive expenses. That is, the term means that an antibody that specifically recognizes a substance contained in a specified ingredient of interest for inspection is supported, retained, or immobilized on an immunochromatograph, for example. Then, when the above-mentioned antibody is bound to an immunochromatograph, the antibody is, for example, retained or directly immobilized on a thin film support such as a cellulose membrane forming the immunochromatograph, or is, for example, retained to a small porous piece such as filter paper bonded to a thin film support.

EXAMPLES

Hereinafter, the present invention is specifically described by way of examples, but those examples are not intended to limit the scope of the present invention.

Test Example 1

Detection of Wheat Gliadin

Each processed food as described in Table 1 below was homogenized with a mixer. To 1 g of the homogenized product, added were 19 ml of an extractant as shown in Table 2 below, and the mixture was shaken at a cycle of about 100 rpm for 12 to 16 hours. The shaken mixture was centrifuged at 3000.times.g for 20 minutes. The supernatant was filtered with filter paper (ADVANTEC No. 5A) (Advantec MFS, Inc., Dublin, Calif.) to prepare a food extract.

The food extract was measured with Morinaga FASPEK wheat measurement kit (gliadin) (manufactured by Morinaga Institute of Biological Science, Inc.). The food extract was diluted by 20-fold with Specimen diluent I in the kit. It should be noted that, when the total wheat protein concentration in the diluted food extract is more than 50 ng/ml, the food extract was further diluted so as to adjust the total wheat protein concentration in the diluted food extract to 1 to 50 ng/ml. After that, 100 μl of the diluted food extract were poured into a plastic well having an immobilized primary antibody, and incubated for 1 hour. The plastic well was washed with a preliminarily prepared washing solution, and then a reaction with an enzyme-labeled antibody was performed for 30 minutes. After that, the plastic well was washed with a preliminarily prepared washing solution, and supplemented with an enzyme substrate solution. After a reaction for 10 minutes, the reaction was terminated with a reaction terminating solution. The absorbances at a main wavelength of 450 nm and a subwavelength of 620 nm were measured within 30 minutes after the termination of the reaction. The total wheat protein concentration in a specimen dilution was determined by applying the measured absorbances to a calibration curve, which had been prepared by a parallel measurement. In addition, the total wheat protein concentration in a sample was determined by multiplying the total wheat protein concentration in a specimen dilution by the dilution magnification. Here, the total wheat protein was measured twice under each condition, and the values in Table 1 below are average values of the measurements (hereinafter, all the results of Test Examples described in this description are each expressed as an average of values obtained from measurement in duplicate.)

TABLE 1

| Processed food | Example 1 | Comparative Example 1-1 | Comparative Example 1-2 |
|---|---|---|---|
| Biscuit "Kyoro-chan cookie (trade name)" manufactured by MORINAGA & CO., LTD. | 36,817 | 31,504 | 6073 |
| Bread (commercially available product) | 72,425 | 81,709 | 16,190 |
| Chocolate confectionery "Chocoball" manufactured by MORINAGA & CO., LTD. | 1450 | 1522 | 683 |

TABLE 1-continued

| Processed food | Example 1 | Comparative Example 1-1 | Comparative Example 1-2 |
|---|---|---|---|
| Stew (roux) (commercially available product) | 20,066 | 16,752 | 7967 |
| Curry (retort) (commercially available product) | 3326 | 3228 | 3.72 |
| Hamburger (retort) (commercially available product) | 5103 | 4663 | 9.59 |

Unit: ppm

TABLE 2

| Extractant No. | Composition |
|---|---|
| Example 1 | Specimen diluent[2] containing 0.5% SDS[1] and 0.1 M $Na_2SO_3$ |
| Comparative Example 1-1 | Specimen diluent containing 0.5% SDS and 2% 2-ME[3] |
| Comparative Example 1-2 | Specimen diluent |

[1]sodium dodecyl sulfate
[2]prepared by diluting a specimen diluent (concentrated by 20-fold) included in "Morinaga FASPEK specified ingredient measurement kit" manufactured by Morinaga Institute of Biological Science, Inc. to 1-fold (corresponding to "Specimen diluent I" in the kit)
[3]2-mercaptoethanol As shown in Table 1, it was clarified that an extractant containing sodium sulfite and SDS exhibited high extraction efficiency compared with an extractant without both agents. Further, the extraction efficiency with the extractant containing sodium sulfite and SDS was almost the same value as that with the extractant containing 2-mercaptoethanol and SDS.

Test Example 2

Detection of Buckwheat Soluble Protein

By the same operation as in Test Example 1, each processed food as described in Table 3 below was used to prepare a food extract from the processed food. Extractants each having a composition shown in Table 2 were used.

The food extract was measured with Morinaga FASPEK buckwheat measurement kit (manufactured by Morinaga Institute of Biological Science, Inc.) to determine the concentration of a buckwheat protein in the same manner as in Test Example 1.

TABLE 3

| Processed food | Example 1 | Comparative Example 1-1 | Comparative Example 1-2 |
|---|---|---|---|
| Boiled buckwheat (commercially available product) | 17,799 | 12,660 | 10,762 |
| Instant pot noodle (buckwheat) (commercially available product) | 14,589 | 12,821 | 7051 |
| Baked confectionery containing buckwheat flour (commercially available product) | 1175 | 1306 | 254 |
| Soft drink (buckwheat tea) (commercially available product) | 2.9 | 2.7 | —* |

Unit: ppm
*below measurement limit

As shown in Table 3, it was clarified that an extractant containing sodium sulfite and SDS exhibited high extraction efficiency compared with an extractant without both agents. Further, the extraction efficiency with the extractant containing sodium sulfite and SDS was almost the same value as that with the extractant containing 2-mercaptoethanol and SDS.

Test Example 3

Detection of Milk Casein by Immunochromatography

A model processed food containing milk casein was prepared by compounding 10 μg of lyophilized milk per g of a processed food ingredient as described below. Each processed food was prepared in accordance with a conventional method.
  Strawberry jam: 58 parts of strawberry, 41 parts of sugars, 0.8 part of pectin, and 0.2 part of citric acid
  Juice: 9 parts of concentrated orange juice, 9 parts of sugar, 0.16 part of citric acid, 0.02 part of ascorbic acid, and 81.8 parts of water
  Biscuit: 67 parts of wheat flour, 6.7 parts of shortening, 13.4 parts of sugar, 0.5 part of salt, 0.9 part of a raising agent, 0.1 part of acida, 0.07 part of an emulsifier, and 0.01 part of a protease In the same manner as in Test Example 1, each sample extract was prepared from the above-mentioned model processed food containing milk casein by using the extractant in Example 1 or Comparative Example 1-1 above. Milk casein in the extract was detected by immunochromatography. Measurement was performed by immunochromatography using a kit for detection of wheat gliadin, "Food allergen inspection kit Nanotrap wheat (gliadin)" (trade name, manufactured by ROHTO Pharmaceutical Co., Ltd.) and a kit for milk casein, "Food allergen inspection kit Nanotrap milk (casein)" (trade name, manufactured by ROHTO Pharmaceutical Co., Ltd.). Specifically, 200 μl of each sample extract diluted by 20-fold were dropped to a sample dropping portion in an immunochromatographic test plate, and after 15 minutes, the presence or absence of band appearance or the contrasting density of the band was observed at a test line position that supports a specific antibody to gliadin or casein. Table 4 shows the results.

TABLE 4

|  |  | Example 1 | Comparative Example 1-1 |
|---|---|---|---|
| Immunochromato (Gliadin) | Strawberry jam | − | ++ |
|  | Juice | − | ++ |
|  | Biscuit | + | ++ |
| Immunochromato (Casein) | Strawberry jam | + | ++ |
|  | Juice | + | ++ |
|  | Biscuit | + | ++ |

(In the table, −, +, and ++ mean, based on the contrasting density of a band that has appeared at an immunochromatographic test line appearance position, −: no band appearance, +: weak band, and ++: strong band)

As shown in Table 4, in the immunochromatography for each sample extract prepared by using an extractant (Comparative Example 1-1) containing 2-mercaptoethanol (2-ME) as a reducing agent, with regard to both of a test plate having a specific antibody to gliadin supported at a test line appearance position, and a test plate having a specific antibody to casein supported at a test line appearance position, a strong band was observed at the test line appearance position. It was clarified that this band was produced by a false positive reaction since such band was also observed in measurement where only an extractant containing 2-mercaptoethanol (2-ME) was dropped to a sample dropping portion.

Meanwhile, in the case of using an extractant (Example 1) containing sodium sulfite ($Na_2SO_3$) as the reducing agent, a positive band was observed at a test line appearance position only in the test plate having a specific antibody to casein supported at a test line appearance position, and no false positive reaction was exhibited.

Thus, in a measurement method using immunochromatography (lateral flow) utilizing an antibody bound to a gold colloid, it was conceivable that a reducing agent (2-mercaptoethanol) having a thiol group caused an aggregation of particles of a gold colloid, latex, or the like with which an antibody had been labeled, resulting in a false positive reaction. In addition, it was revealed that the use of sodium sulfite ($Na_2SO_3$) allowed the false positive reaction to be avoided, leading to accurate detection.

The results of Test Examples 1 to 3 above revealed that a sulfite that was inexpensive and had a mild reducing action was useful as a reducing agent for extracting a component from a food.

Test Example 4

Detection of Wheat Gliadin

In order to evaluate, during measurement of wheat gliadin by immunochromatography, how the measurement is affected by the presence of sodium dodecyl sulfate (SDS) and sodium sulfite in a test solution, the following test was performed.

First, to 1 g of wheat flour, added were 19 ml of an extractant as shown in Table 5 below, and the mixture was stirred with a vortex mixer at its maximum speed for 1 minute. The resultant was boiled at 100.degree. C. for 10 minutes, returned to a normal temperature, and then centrifuged at 3000.times.g for 20 minutes. The supernatant was filtered with filter paper (ADVANTEC No. 5A) (Advantec MFS, Inc., Dublin, Calif.) to prepare a wheat flour extract. With regard to the wheat flour extract, the concentration was separately determined by an ELISA method using Morinaga FASPEK wheat measurement kit (gliadin) (manufactured by Morinaga Institute of Biological Science, Inc.). A specific procedure is as described below.

That is, the wheat flour extract was diluted by 20-fold with Specimen diluent I in the kit. It should be noted that, when the total wheat protein concentration in the dilution is more than 50 ng/ml, the wheat flour extract was further diluted so as to adjust the total wheat protein concentration to 1 to 50 ng/ml. After that, 100 μl of the subject specimen were poured into a plastic well having an immobilized primary antibody, and incubated for 1 hour. The plastic well was washed with a preliminarily prepared washing solution, and then a reaction with an enzyme-labeled antibody was performed for 30 minutes. After that, the plastic well was washed with a preliminarily prepared washing solution, and supplemented with an enzyme substrate solution. After a reaction for 10 minutes, the reaction was terminated with a reaction terminating solution. The absorbances at a main wavelength of 450 nm and a subwavelength of 620 nm were measured within 30 minutes after the termination of the reaction. The total wheat protein concentration in the subject specimen was determined by applying the measured absorbances to a calibration curve, which had been prepared by a parallel measurement using the total wheat protein as a standard substance. In addition, the total wheat protein concentration in the wheat flour extract was determined by multiplying the total wheat protein concentration in the subject specimen by the dilution magnification.

Hereinafter, the wheat flour extract was used as a standard.
The standard of the wheat flour extract as described above was serially diluted in the range of 1 ng to 100 μg by using a standard diluent (5-fold dilution of extractant) of Example 2 containing SDS and a sulfite as shown in Table 5 below. Further, for the purpose of comparison, serial dilutions using a standard diluent of Comparative Example 2 without SDS and a sulfite as shown in Table 5 below were also prepared.

TABLE 5

| | Composition |
|---|---|
| (Extractant) | Specimen diluent[2] containing 0.6% SDS[1] and 0.1 M $Na_2SO_3$ |
| (Standard diluent) | |
| Example 2 | Specimen diluent[2] containing 0.12% SDS[1] and 0.02 M $Na_2SO_3$ |
| Comparative Example 2 | Specimen diluent[2] |

[1]sodium dodecyl sulfate
[2]prepared by diluting a specimen diluent (concentrated by 20-fold) included in "Morinaga FASPEK specified ingredient measurement kit" manufactured by Morinaga Institute of Biological Science, Inc. to 1-fold (corresponding to "Specimen diluent I" in the kit)

Those serial dilutions were measured with a kit for immunochromatographic measurement of wheat gliadin, "Morinaga specified ingredient immunochromatographic method kit Nanotrap series (wheat)" (trade name, manufactured by Morinaga Institute of Biological Science, Inc.). That is, 200 μL each of the above-mentioned serial dilutions as test solutions were dropped to a sample dropping portion in a stick, and after about 15 minutes, the presence or absence of band appearance or the contrasting density of the band was visually observed at a test line position that supports a specific antibody to gliadin. Further, the intensity of the band was measured by using a measuring instrument utilizing optical reflection, "Immunochromato Reader 010066" (product name, manufactured by Hamamatsu Photonics K.K.) and expressed as a numerical value, that is, an mABS value (absorbance). Table 6 shows those results collectively. In addition, FIG. 1 is a graph illustrating, as a numerical value, the intensity of the band.

TABLE 6

| | Standard diluent | | | |
|---|---|---|---|---|
| | Containing SDS/sulfite (Example 2) | | Without SDS/sulfite (Comparative Example 2) | |
| SDS/sulfite Gliadin concentration (ng/mL) | mABS | Visual observation | mABS | Visual observation |
| blank | 0.0 | − | 7.0 | − |
| 1 ng/mL | 5.2 | − | 4.0 | − |
| 10 ng/mL | 42.1 | ± | 38.3 | ± |
| 50 ng/mL | 115.8 | + | 98.8 | + |
| 100 ng/mL | 157.6 | + | 58.6 | +* |
| 1 μg/mL | 192.6 | + | 70.0 | +* |
| 10 μg/mL | 92.6 | + | 30.7 | ±* |
| 100 μg/mL | 48.2 | ± | 7.0 | − |

*It was difficult to make an assessment because a membrane was colored red.

As shown in Table 6 or FIG. 1, in a system (Comparative Example 2) using a test solution without SDS and sodium sulfite, when the gliadin concentration reached around 50 to 100 ng/mL, an mABS value was lowered, a prozone phenomenon was observed, and it became difficult to make an assessment on the contrasting density of the band because a membrane itself was colored red. Further, when the gliadin concentration reached 100 μg/mL, it became impossible to recognize the band, resulting in false negative results. On the other hand, in a system (Example 2) using a test solution containing SDS and sodium sulfite, it became possible to recognize the band when the gliadin concentration reached around 10 ng/mL, no prozone phenomenon occurred even when the gliadin concentration reached around 1 μg/mL, and further, it did not become difficult to make an assessment on the contrasting density of the band before the gliadin concentration reached 100 μg/mL.

Thus, it was clarified that, during detection of wheat gliadin by immunochromatography, more reliable measurement can be performed in an SDS/sulfite system in a wide range of concentration regions.

Test Example 5

Detection of Milk Casein

In order to evaluate, during measurement of milk casein by immunochromatography, how the measurement is affected by the presence of sodium dodecyl sulfate (SDS) and sodium sulfite in a test solution, the following test was performed.

First, to 1 g of milk, added were 19 ml of an extractant as shown in Table 7 below, and the mixture was stirred with a vortex mixer at its maximum speed for 1 minute. The resultant was boiled at 100.degree. C. for 10 minutes, returned to a normal temperature, and then centrifuged at 3000.times.g for 20 minutes. The supernatant was filtered with filter paper (ADVANTEC No. 5A) (Advantec MFS, Inc., Dublin, Calif.) to prepare a milk extract. With regard to the milk extract, the concentration was separately determined by an ELISA method using Morinaga FASPEK milk measurement kit (casein) (manufactured by Morinaga Institute of Biological Science, Inc.). A specific procedure is as described below.

That is, the milk extract was diluted by 20-fold with Specimen diluent I in the kit. It should be noted that, when the total milk protein concentration in the dilution is more than 50 ng/ml, the milk extract was further diluted so as to adjust the total milk protein concentration to 1 to 50 ng/ml. After that, in the same manner as in Test Example 4, the total milk protein in a subject specimen was determined, and further, the total milk protein in the milk extract was determined by multiplying the total milk protein in the subject specimen by the dilution magnification.

Hereinafter, the milk extract was used as a standard.

The standard of the milk extract as described above was serially diluted in the range of 1 ng to 100 μg by using a standard diluent (5-fold dilution of extractant) of Example 3 containing SDS and a sulfite as shown in Table 7 below. Further, for the purpose of comparison, serial dilutions using a standard diluent of Comparative Example 3 without SDS and a sulfite as shown in Table 7 below were also prepared.

TABLE 7

| | Composition |
|---|---|
| (Extractant) | Specimen diluent[2] containing 0.6% SDS[1] and 0.1 M $Na_2SO_3$ |
| (Standard diluent) | |
| Example 3 | Specimen diluent[2] containing 0.12% SDS[1] and 0.02 M $Na_2SO_3$ |
| Comparative Example 3 | Specimen diluent[2] |

[1]sodium dodecyl sulfate
[2]prepared by diluting a specimen diluent (concentrated by 20-fold) included in "Morinaga FASPEK specified ingredient measurement kit" manufactured by Morinaga Institute of Biological Science, Inc. to 1-fold (corresponding to "Specimen diluent I" in the kit)

Those serial dilutions were measured with a kit for immunochromatographic measurement of milk casein, "Morinaga specified ingredient immunochromatographic method kit Nanotrap series (milk)" (trade name, manufactured by Morinaga Institute of Biological Science, Inc.). That is, 200 μL each of the above-mentioned serial dilutions as test solutions were dropped to a sample dropping portion in a stick, and after about 15 minutes, the presence or absence of band appearance or the contrasting density of the band was visually observed at a test line position that supports a specific antibody to casein. Further, the intensity of the band was measured by using a measuring instrument utilizing optical reflection, "Immunochromato Reader C10066" (product name, manufactured by Hamamatsu Photonics K.K.) and expressed as a numerical value, that is, an mABS value (absorbance). Table 8 shows those results collectively. In addition, FIG. 2 is a graph illustrating, as a numerical value, the intensity of the band.

TABLE 8

| SDS/sulfite Casein concentration (ng/mL) | Standard diluent | | | |
|---|---|---|---|---|
| | Containing SDS/sulfite (Example 3) | | Without SDS/sulfite (Comparative Example 3) | |
| | mABS | Visual observation | mABS | Visual observation |
| blank | — | — | — | — |
| 1 ng/mL | 4.6 | — | 12.9 | — |
| 10 ng/mL | 15.1 | — | 37.1 | ± |
| 50 ng/mL | 88.9 | + | 185.7 | + |
| 100 ng/mL | 129.0 | + | 243.5 | + |
| 1 µg/mL | 174.1 | + | 233.5 | + |
| 10 µg/mL | 149.6 | + | 51.7 | ± |
| 100 µg/mL | 131.2 | + | 7.0 | + |

As shown in Table 8 or FIG. 2, in a system (Comparative Example 3) using a test solution without SDS and sodium sulfite, when the casein concentration reached around 1 to 10 µg/mL, an mABS value was lowered, and a prozone phenomenon was observed. Further, when the casein concentration reached 100 µg/mL, it became impossible to recognize the band, resulting in false negative results. On the other hand, in a system (Example 3) using a test solution containing SDS and sodium sulfite, it became possible to recognize the band when the gliadin concentration reached around 50 ng/mL, no prozone phenomenon occurred even when the casein concentration reached around 100 µg/mL, and further, it did not become difficult to make an assessment on the contrasting density of the band before the casein concentration reached 100 µg/mL.

Thus, it was clarified that, during detection of milk casein by immunochromatography, more reliable measurement can be performed in an SDS/sulfite system in a wide range of concentration regions.

Test Example 6

Detection of Wheat Gliadin Contained in Food

Each of foods as described in Table 9 below was homogenized with a mixer.

TABLE 9

| | Ingredient labeling of wheat ingredient in product |
|---|---|
| Soft flour | Positive food (unheated) ○ |
| Curry roux (commercially available product) | Positive food (heated) ○ |
| Roux for rice with hashed meat (retort) (commercially available product) | |

TABLE 9-continued

| | Ingredient labeling of wheat ingredient in product |
|---|---|
| Stir-fried chicken with cashewnuts (retort) (commercially available product) | ○ |
| Biscuit (commercially available product) | ○ |
| Consomme cube (commercially available product) | ○ |
| Pudding (commercially available product) | ○ |
| Meatball (retort) (commercially available product) | Negative food — |
| Rice gruel (retort) (commercially available product) | — |
| Neapolitan sauce (retort) (commercially available product) | — |
| Baked tube-shaped fish-paste cake (commercially available product) | — |
| Raw eggs | Negative ingredient (five items) — |
| Milk | — |
| Buckwheat | — |
| Peanuts | — |

To 1 g of the homogenized food, added were 19 ml of the extractant of Example 4 as shown in Table 10 below, and the mixture was stirred with a vortex mixer at its maximum speed for 1 minute. The resultant was boiled at 100.degree. C. for 10 minutes, returned to a normal temperature, then centrifuged at 3000.times.g for 20 minutes. The supernatant was filtered with filter paper (ADVANTEC No. 5A) (Advantec MFS, Inc., Dublin, Calif.) to prepare a food extract. Further, for the purpose of comparison, food extracts using an extractant of Comparative Example 4 without SDS and a sulfite as shown in Table 10 below were also prepared.

Each of the food extracts as described above was diluted by 5-fold with a test solution diluent without SDS and sulfite as shown in Table 10 below (being the same as the standard diluent used in Test Example 4 or 5) to prepare a test solution, which is subjected to the following immunochromatography. Further, with regard to those food extracts, the concentration was separately determined by the ELISA method using Morinaga FASPEK wheat measurement kit (gliadin) (manufactured by Morinaga Institute of Biological Science, Inc.) in the same manner as in Test Example 4.

TABLE 10

| (Extractant) | Composition |
|---|---|
| Example 4 | Specimen diluent[2] containing 0.6% SDS[1] and 0.1 M Na$_2$SO$_3$ |
| Comparative Example 4 (Test solution diluent) | Specimen diluent[2] Specimen diluent[2] |

[1]sodium dodecyl sulfate
[2]prepared by diluting a specimen diluent (concentrated by 20-fold) included in "Morinaga FASPEK specified ingredient measurement kit" manufactured by Morinaga Institute of Biological Science, Inc. to 1-fold (corresponding to "Specimen diluent I" in the kit)

Test solutions prepared as described above were measured with a kit for immunochromatographic measurement of wheat gliadin, "Morinaga specified ingredient immunochromatographic method kit Nanotrap series (wheat)" (trade name, manufactured by Morinaga Institute of Biological Science, Inc.). That is, 200 µL each of the above-mentioned test solutions were dropped to a sample dropping portion, and after about 15 minutes, the presence or absence of band appearance or the contrasting density of the band was visually observed at a test line position that supports a specific antibody to gliadin. Table 11 collectively shows the measurement results of the gliadin concentration measured by the ELISA method and immunochromatographic measurement results.

TABLE 11

| | SOS/sulfite | Ingredient labeling of wheat ingredient | Extractant Containing SOS/sulfite (Example 4) Concentration value measured by ELISA method | Visual observation | Without SOS/sulfite (Comparative Example 4) Concentration value measured by ELISA method | Visual observation |
|---|---|---|---|---|---|---|
| Soft flour | | Positive food (unheated) | 20.5 mg/mL | -* | 472 ug/mL | -* |
| Curry roux (commercially available product) | | Positive food (heated) | >400 ug/mL | + | 126 ug/mL | -* |
| Roux for rice with hashed meat (retort) (commercially available product) | | | >400 ug/mL | + | 1.3 ug/mL | -* |
| Stir-fried chicken with cashew nuts (retort) (commerciallly available product) | | | 400 ng/mL | + | N.D. | - |
| Biscuit (commercially available product) | | | >400 ug/mL | ± | 252 ug/mL | -* |
| Consomme cube (commercially available product) | | | >400 ug/mL | + | N.D. | - |
| Pudding (commercially available product) | | | N.D. | - | N.D. | - |
| Meatball (retort) (commercially available product) | Negative food | | 18 ng/mL | - | N.D. | - |
| Rice gruel (retort) (commercially available product) | | | N.D. | - | N.D. | - |
| Neopolitan sauce (retort) (commercially available product) | | | N.D. | - | N.D. | - |
| Baked tube-shaped fish-paste cake (commercially available product) | | | N.D. | - | N.D. | - |
| Raw eggs | Negative food (five items) | | N.D. | - | N.D. | - |
| Milk | | | N.D. | - | N.D. | - |
| Buckwheat | | | Not measured | - | N.D. | - |
| Peanuts | | | Not measured | - | N.D. | - |

*indicates a prozone phenomenon.

 Samples in each of which any improvement in detection was observed

As shown in Table 11, a system (Comparative Example 4) using a test solution without SDS and sodium sulfite gave false negative immunochromatographic measurement results in "Soft flour", "Curry roux (commercially available product)", "Roux for rice with hashed meat (retort) (commercially available product)", and "Biscuit (commercially available product)", all of which have an ingredient labeling of wheat ingredient on packages of their commercially available products. On the other hand, a system (Example 4) using a test solution containing SDS and sodium sulfite gave positive results in "Curry roux (commercially available product)", "Roux for rice with hashed meat (retort) (commercially available product)", "Stir-fried chicken with cashew nuts (retort) (commercially available product)", "Biscuit (commercially available product)", and "Consomme cube (commercially available product)" as indicated by ingredient labeling of wheat ingredient on packages of their commercially available products. It should be noted that "Soft flour" containing gliadin in a concentration as high as 20.5 mg/mL, which has been measured by the ELISA method, gave false negative results owing to a prozone phenomenon. Further, although "Pudding (commercially available product)" has ingredient labeling of wheat ingredient on a package of its commercially available product, no gliadin was detected in both systems. Therefore, the concentration of gliadin contained in the product was considered to be relatively slight.

Those results revealed that, during inspection of the presence or absence and/or the amount of a wheat ingredient in a food by immunochromatography, an SDS/sulfite system allowed more reliable measurement in a wide range of concentration regions.

Test Example 7

Detection of Milk Casein Contained in Food

Each of foods as described in Table 12 below was homogenized with a mixer.

TABLE 12

| | | Ingredient labeling of Milk ingredient in product |
|---|---|---|
| Milk | Positive food (unheated) | o |
| Consomme cube (commercially available product) | Positive food (heated) | o |
| Roux for rice with hashed meat (retort) (commercially available product) | | o |
| Pudding (commercially available product) | | o |
| Stir-fried chicken with cashew nuts (retort) (commercially available product) | Negative food | — |
| Biscuit (commercially available product) | | — |
| Meatball (retort) (commercially available product) | | — |

TABLE 12-continued

| | | Ingredient labeling of Milk ingredient in product |
|---|---|---|
| Rice gruel (retort) (commercially available product) | | — |
| Neapolitan sauce (retort) (commercially available product) | | — |
| Raw eggs | Negative food (five items) | — |
| Soft flour | | — |
| Buckwheat | | — |
| Peanuts | | — |

To 1 g of the homogenized food, added were 19 ml of the extractant of Example 5 as shown in Table 13 below, and the mixture was stirred with a vortex mixer at its maximum speed for 1 minute. The resultant was boiled at 100.degree. C. for 10 minutes, returned to a normal temperature, then centrifuged at 3000.times.g for 20 minutes. The supernatant was filtered with filter paper (ADVANTEC No. 5A) (Advantec MFS, Inc., Dublin, Calif.) to prepare a food extract. Further, for the purpose of comparison, food extracts using an extractant of Comparative Example 5 without SDS and a sulfite as shown in Table 13 below were also prepared.

Each of the food extracts as described above was diluted by 5-fold with a test solution diluent without SDS and sulfite as shown in Table 13 below (being the same as the standard diluent used in Test Example 4 or 5) to prepare a test solution, which is subjected to the following immunochromatography. Further, with regard to those food extracts, the concentration was separately determined by the ELISA method using Morinaga FASPEK milk measurement kit (casein) (manufactured by Morinaga Institute of Biological Science, Inc.) in the same manner as in Test Example 5.

TABLE 13

| (Extractant) | Composition |
|---|---|
| Example 5 | Specimen diluent[2] containing 0.6% SDS[1] and 0.1 M $Na_2SO_3$ |
| Comparative Example 5 (Test solution diluent) | Specimen diluent[2] Specimen diluent[2] |

[1]sodium dodecyl sulfate
[2]prepared by diluting a specimen diluent (concentrated by 20-fold) included in "Morinaga FASPEK specified ingredient measurement kit" manufactured by Morinaga Institute of Biological Science, Inc. to 1-fold (corresponding to "Specimen diluent I" in the kit)

Test solutions prepared as described above were measured with a kit for immunochromatographic measurement of milk casein, "Morinaga specified ingredient immunochromatographic method kit Nanotrap series (milk)" (trade name, manufactured by Morinaga Institute of Biological Science, Inc.). That is, 200 μL each of the above-mentioned test solutions were dropped to a sample dropping portion, and after about 15 minutes, the presence or absence of band appearance or the contrasting density of the band was visually observed at a test line position that supports a specific antibody to casein. Table 14 collectively shows the measurement results of the casein concentration measured by the ELISA method and immunochromatographic measurement results.

TABLE 14

| | | | Extractant | | | |
|---|---|---|---|---|---|---|
| | | SOS/sulfite | Containing SOS/sulfite (Example 5) | | Without SOS/sulfite (Comparative Example 5) | |
| | | Milk ingredient Ingredient labeling | Concentration value measured by ELISA method | Visual observation | Concentration value measured by ELISA method | Visual observation |
| Milk | Positive food (unheated) | o | 2.6 mg/mL | + | 1.22 mg/mL | -* |
| Consomme cube (commercially available product) | Positive food (heated) | o | N.D. | - | 36 ng/mL | - |
| Roux for rice with hashed meat (retort) (commercially available product) | | o | 38.4 ug/mL | + | 158 ng/mL | + |
| Pudding (commercially available product) | | o | 832 ng/mL | + | 259 ug/mL | -* |
| Stir-fried chicken with cashew nuts (retort) (commerciallly available product) | Negative food | | N.D. | - | N.D. | - |
| Biscuit (commercially available product) | | | 40 ng/mL | ± | N.D. | ± |
| Meatball (retort) (commercially available product) | | | N.D. | - | N.D. | - |
| Rice gruel (retort) (commercially available product) | | | N.D. | - | N.D. | - |
| Neopolitan sauce (retort) (commercially available product) | | | N.D. | - | N.D. | - |
| Raw eggs | Negative food (five items) | | N.D. | - | N.D. | - |
| Soft flour | | | N.D. | - | N.D. | - |
| Buckwheat | | | Not measured | - | N.D. | - |
| Peanuts | | | Not measured | - | N.D. | - |

*indicates a prozone phenomenon.
▒ Samples in each of which any improvement in detection was observed As shown in Table 14, a system (Comparative Example 5) using a test solution without SDS and sodium sulfite gave false negative immunochromatographic measurement results in "Milk" and "Pudding (commercially available product)", all of which have an ingredient labeling of milk ingredient on packages of their commercially available products. On the other hand, a system (Example 5) using a test solution containing SDS and sodium sulfite gave positive results in "Milk", "Roux for rice with hashed meat (retort) (commercially available product)", and "Pudding (commercially available product)" as indicated by ingredient labeling of milk ingredient on packages of their commercially available products. It should be noted that, a' though "Consomme cube (commercially available product)" has ingredient labeling of milk ingredient on a package of its commercially available product, the concentration value measured by the ELISA method was equal to or less than the detection limit (in the case of the extractant of Example 5) or was 36 ng/mL (in the case of the extractant of Comparative Example 5). Therefore, the concentration of casein contained in the product was considered to be relatively slight.

Those results revealed that, during inspection of the presence or absence and/or the amount of a milk ingredient in a food by immunochromatography, an SDS/sulfite system allowed more reliable measurement in a wide range of concentration regions.

Test Example 8

Evaluation on Individual Influence by SDS or Sodium Sulfite

In order to examine which of SDS and sodium sulfite nitrite mainly exhibits an action and effect of suppressing a prozone phenomenon, a test was performed by using a standard diluent as shown in Table 15 below in the same manner as in Test Example 4 (gliadin) or Test Example 5 (casein) above.

TABLE 15

| (Standard diluent) | Composition |
|---|---|
| Example 6 | Specimen diluent[2] containing 0.12% SDS[1] and 0.02 M $Na_2SO_3$ |
| Example 7 | Specimen diluent[2] containing 0.12% SDS[1] |
| Comparative Example 6 | Specimen diluent[2] containing 0.02 M $Na_2SO_3$ |
| Comparative Example 7 | Specimen diluent[2] |

[1] sodium dodecyl sulfate
[2] prepared by diluting a specimen diluent (concentrated by 20-fold) included in "Morinaga FASPEK specified ingredient measurement kit" manufactured by Morinaga Institute of Biological Science, Inc. to 1-fold (corresponding to "Specimen diluent I" in the kit)

Tables 16 and 17 shows the results collectively.

TABLE 16

| Gliadin concentration (ng/mL) | SDS/sulfite (Example 6) | SDS (Example 7) | Sulfite (Comparative Example 6) | Control (Comparative Example 7) |
|---|---|---|---|---|
| blank | − | − | − | − |
| 1 ng/mL | − | − | − | − |
| 10 ng/mL | ± | ± | ± | ± |
| 100 ng/mL | + | + | +* | +* |
| 1 µg/mL | + | + | +* | +* |
| 10 µg/mL | + | + | ±* | ±* |
| 100 µg/mL | + | + | − | − |

*It was difficult to make an assessment because a membrane was colored red.

TABLE 17

| Casein concentration (ng/mL) | SDS/sulfite (Example 6) | SDS (Example 7) | Sulfite (Comparative Example 6) | Control (Comparative Example 7) |
|---|---|---|---|---|
| blank | − | − | − | − |
| 1 ng/mL | − | − | − | − |
| 10 ng/mL | − | − | − | − |
| 100 ng/mL | ± | ± | ± | ± |
| 1 µg/mL | + | + | + | + |
| 10 µg/mL | + | + | + | + |
| 100 µg/mL | + | + | ± | ± |
| 1 mg/mL | ± | | | − |

As a result, as clear from Tables 16 and 17, since Example 7 containing only SDS could detect gliadin and casein even in highly concentrated regions similarly to Example 6 containing SDS and a sulfite as the suppressor for a prozone phenomenon, it was shown that the presence of SDS in a test solution, which was subjected to immunochromatography, suppressed a prozone phenomenon. Accordingly, in SDS and sodium sulfite used in Test Examples 4 to 7 above, SDS was considered to mainly exhibit an action and effect of suppressing a prozone phenomenon. Institute of Biological Science, Inc. to 1-fold (corresponding to "Specimen diluent I" in the kit)

Figure 1:
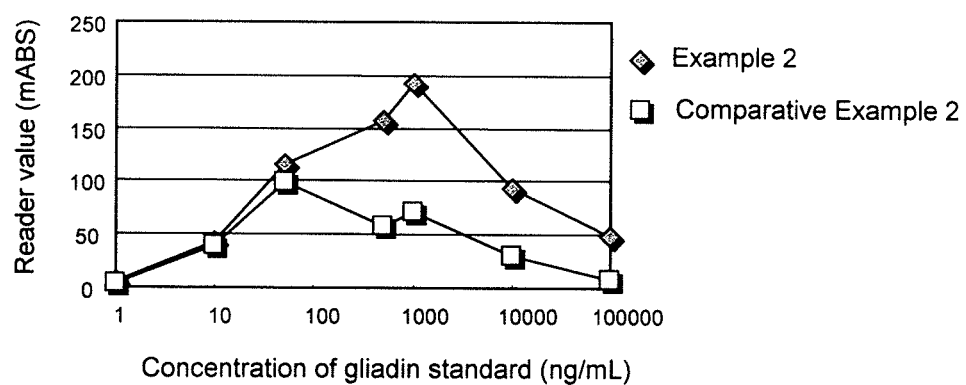
FIG. 1 is a graph illustrating, as a numerical value, an intensity of a band at a test line position that supports a specific antibody to gliadin in immunochromatography.
Figure 2:
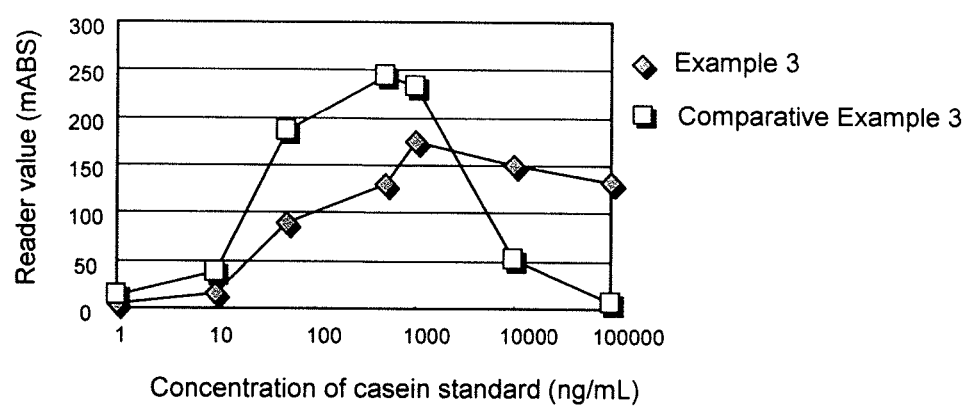
FIG. 2 is a graph illustrating, as a numerical value, an intensity of a band at a test line position that supports a specific antibody to casein in immunochromatography.

The invention claimed is:

1. A food inspection method for inspection of a presence or absence and/or an amount of a specified ingredient in a food, comprising: bringing a food into contact with an extractant comprising 0.0001 to 1M of sulfite and 0.01 to 10 w/v % of sodium dodecyl sulfate (SDS) to prepare a food extract in which a component in the food is extracted; then bringing the food extract into contact with a specific antibody that specifically recognizes a substance comprised in a specified ingredient of interest for inspection; and inspecting a presence or absence and/or an amount of the specified ingredient in the food by immunochromatography or ELISA.

2. The food inspection method according to claim 1, wherein the specific antibody is labeled with a metal colloid.

3. The food inspection method according to claim 1, wherein the sulfite is selected from the group consisting of sodium sulfite, sodium hydrogen sulfite, potassium sulfite, ammonium sulfite, and iron sulfite.

4. The food inspection method according to claim 1, wherein: the specified ingredient of interest for inspection comprises wheat; and the specific antibody comprises a specific antibody to gliadin.

5. The food inspection method according to claim 4, wherein the food extract, which is subjected to the immunochromatography, comprises gliadin in a concentration of 10 ng/ml to 100 μg/ml.

6. The food inspection method according to claim 1, wherein: the specified ingredient of interest for inspection comprises milk; and the specific antibody comprises a specific antibody to casein.

7. The food inspection method according to claim 6, wherein the food extract, which is subjected to the immunochromatography, comprises casein in a concentration of 50 ng/ml to 100 μg/ml.

* * * * *